United States Patent [19]

Dren et al.

[11] 4,292,316
[45] Sep. 29, 1981

[54] ANTIGLAUCOMA AGENTS

[75] Inventors: Anthony T. Dren, Waukegan; Barbara A. Bopp, Lake Bluff, both of Ill.

[73] Assignee: Abbott Laboratories, North Chicago, Ill.

[21] Appl. No.: 112,989

[22] Filed: Jan. 17, 1980

Related U.S. Application Data

[62] Division of Ser. No. 948,058, Oct. 2, 1978, Pat. No. 4,217,351, which is a division of Ser. No. 711,749, Aug. 4, 1976, Pat. No. 4,136,183.

[51] Int. Cl.³ .................. A61K 27/00; A61K 31/54; A61K 31/495; A61K 31/445
[52] U.S. Cl. .................. 424/248.56; 424/244; 424/246; 424/250; 424/256; 424/263; 424/267; 424/272; 424/273 R; 424/274; 424/283
[58] Field of Search ........... 424/248.56, 244, 256, 424/263, 272, 273 R, 250, 267, 246, 274, 283

[56] References Cited

U.S. PATENT DOCUMENTS

| | | | |
|---|---|---|---|
| 3,901,926 | 8/1975 | Winn et al. | 424/263 |
| 3,941,782 | 3/1976 | Harris et al. | 424/283 |
| 4,025,630 | 5/1977 | Dren et al. | 424/256 |

Primary Examiner—Douglas W. Robinson
Attorney, Agent, or Firm—Gildo E. Fato; Robert L. Niblack

[57] ABSTRACT

A method of reducing intra-ocular pressure in mammalian patients comprising administering to a glaucoma patient a therapeutically effective amount of a compound of the formula

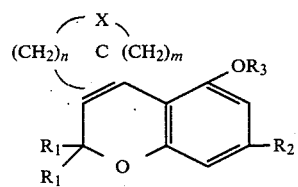

wherein, in the C ring, X is $CH_2$, S,

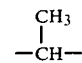

or $NR_4$ where $R_4$ is H, loweralkyl, loweralkenyl, loweralkynyl or loweralkanoyl; n is an integer of 0 to 3; m is an integer of 0 to 3, or the C ring is a quinuclidine ring

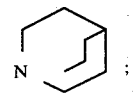

each $R_1$ is loweralkyl, and when taken together, the substituents $R_1R_1$ form oxygen; $R_2$ is a $C_1$-$C_{20}$ straight or branched chain alkyl, cycloalkyl, or

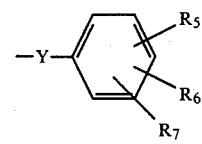

wherein Y is a straight or branched chain alkylene group having from 1 to 10 carbon atoms, and each $R_5$, $R_6$ and $R_7$ are the same or different members of the group consisting of H, halo or loweralkyl; $R_3$ is H or

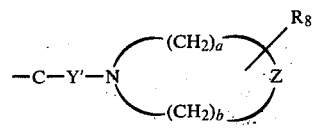

wherein Y' is a straight or branched chain alkylene group having 1 to 8 carbon atoms, a is an integer from 1 to 4, b is an integer from 1 to 4, Z is $CH_2$, O, S or $NR_9$ where $R_9$ is H or loweralkyl, with the provision that when Z is O, S or $NR_9$, the sum of a and b is 3 or 4, and $R_8$ is H or loweralkyl; and the pharmaceutically acceptable salts thereof.

3 Claims, No Drawings

ANTIGLAUCOMA AGENTS

This application is a division of application Ser. No. 948,058, Feb. 2, 1978, now U.S. Pat. No. 4,217,351, issued on Aug. 12, 1980, which is a division of Ser. No. 711,749, Aug. 4, 1976, U.S. Pat. No. 4,136,183, issued Jan. 23, 1979.

BACKGROUND OF THE INVENTION

This invention relates to the disease of glaucoma. Glaucoma is a disease of the eye, characterized by an increase of intra-ocular pressure and impaired vision. In the adult, there are two types of glaucoma: (1) primary glaucoma which may be a wide angle or a narrow angle, and (2) secondary glaucoma which is a result of ocular disease. The major treatment for glaucoma is the use of miotic agents which constrict the pupil and allow for better drainage. When the human eye has the disease of glaucoma, it is marked by an intense intra-ocular pressure, resulting in hardness of the eye, atrophy of the retina, cupping of optic disc and blindness. The problem is that if the glaucoma is not treated and the symptoms reduced, blindness may result.

Glaucoma is responsible for about 14% of all new reported blindness cases, and thus represents a significant economical problem which must be treated either medically or surgically. Various medications are currently available, but only a few are widely used, and the addition of another highly effective drug to the ophthalmological armemtarium would provide a greater choice for medical therapy.

The present invention provides such drugs which are effective as antiglaucoma agents, i.e., effective in reducing the intra-ocular pressure in mammalian patients.

DETAILED DESCRIPTION OF THE INVENTION

This invention relates to an improved method of reducing the intra-ocular pressure in mammalian patients comprising administering to a glaucoma patient a therapeutically effective amount of a compound of the formula I

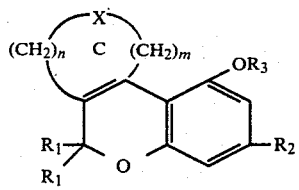

wherein, in the C ring, X is $CH_2$, S,

or $NR_4$ where $R_4$ is H, loweralkyl, loweralkenyl, loweralkynyl or loweralkanoyl; n is an integer of 0 to 3; m is an integer of 0 to 3, or the C ring is a quinuclidine ring

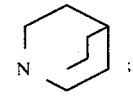

each $R_1$ is loweralkyl, and when taken together, the substituents $R_1R_1$ form oxygen; $R_2$ is a $C_1$–$C_{20}$ straight or branched chain alkyl, cycloalkyl, or

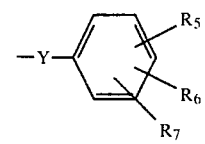

wherein Y is a straight or branched chain alkylene group having from 1 to 10 carbon atoms, and each $R_5$, $R_6$ and $R_7$ are the same or different members of the group consisting of H, halo or loweralkyl; $R_3$ is H or

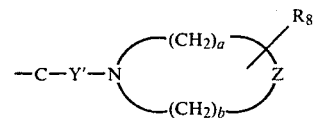

wherein Y' is a straight or branched chain alkylene group having 1 to 8 carbon atoms, a is an integer from 1 to 4, b is an integer from 1 to 4, Z is $CH_2$, O, S or $NR_9$ where $R_9$ is H or loweralkyl, with the provision that when Z is O, S or $NR_9$, the sum of a and b is 3 or 4, and $R_8$ is H or loweralkyl; and the pharmaceutically acceptable salts thereof.

As used herein, the term "loweralkyl" refers to $C_1$–$C_6$ straight or branched chain alkyl groups including methyl, ethyl, n-pentyl, iso-pentyl, neo-pentyl, n-propyl, iso-propyl, n-butyl, sec-butyl, tert-butyl, n-hexyl and the like.

The term "loweralkenyl" refers to straight and branched chain $C_2$–$C_6$ alkyl radicals from which a hydrogen atom has been removed from each of two adjacent carbon atoms to produce ethylenic unsaturation; e.g., vinyl, allyl, methallyl, 1-pentenyl and the like.

The term "loweralkynyl" refers to $C_2$–$C_6$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like groups.

The term "halo" includes chloro, fluoro, bromo and iodo.

The term "loweralkanoyl" refers to saturated monovalent, aliphatic radicals derived from a monocarboxylic acid, including straight or branched chain radicals of from one to six carbon atoms including the formyl, acetyl, propionyl, α-methylpropionyl, butyryl, hexanoyl and the like radicals.

"Cycloalkyl", as used herein, refers to cyclic saturated aliphatic radicals having three to eight carbon atoms in a ring, such as cyclopropyl, cyclobutyl, cyclopentyl, cyclohexyl, cycloheptyl and cyclooctyl.

"Cycloalkylloweralkyl" refers to groups such as cyclopropyl-methyl, 2-methylcyclobutyl and the like.

The term "alkyl" refers to straight and branched chain alkyl radicals having from one to twenty carbon atoms such as methyl, n-amyl, 3-methyl-2-octyl, 2-nonyl, 2-eicosanyl and the like.

The term "pharmaceutically acceptable acid addition salts" refers to non-toxic salts prepared by reacting the basic esters of the benzopyranopyridines with an organic or inorganic acid, or by reacting the benzopyranopyridines with the salt of an appropriate acid. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like.

When $R_3$ is hydrogen, the term "pharmaceutically acceptable salts" refers to the alkali earth, alkali metal, ammonia and substituted ammonium salts such as the sodium, potassium, aluminum, magnesium, benzylammonium, methylammonium, dimethylammonium and the like salts.

The following formulae illustrate the compounds useful in the practice of this invention.

When X is $NR_4$ and n is 3, the compounds useful in the practice of this invention are represented by formula II.

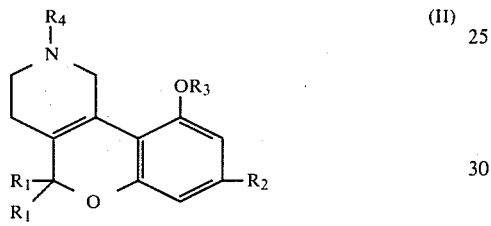

When the C ring is a quinuclidine ring and $R_1R_1=O$, the compounds are represented by formula (III).

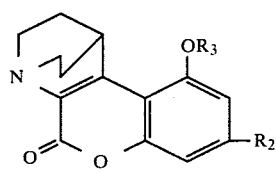

When $R_3$ is hydrogen and X is $NR_4$ where $R_4$ is loweralkyl, the compounds are prepared according to U.S. Pat. No. 3,576,798. When $R_3$ is

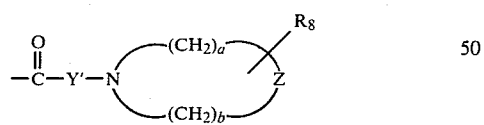

the corresponding esters are prepared by equimolar amounts of the phenolic benzopyranopyridines with an appropriate acid or salt thereof in the presence of a carbodiimide such as dicyclohexyl carbodiimide and a suitable solvent such as methylene chloride, chloroform and the like. This reaction can be represented as follows:

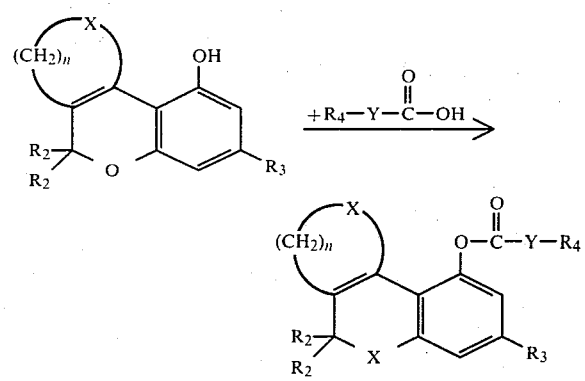

Some of the heterocyclic acids which can be used in the process of preparing the esters of this invention are:
γ-piperidinobutyric acid,
γ-morpholinobutyric acid,
γ-(2-methylpiperidino)-butyric acid,
δ-piperidininovaleric acid,
γ-pyrrolidinobutyric acid,
β-piperidinopropionic acid,
γ-thiomorpholinobutyric acid, and
homopiperidinoacetic acid.

Reaction between the benzopyran starting material and the heterocyclic acid, or salt thereof, is readily effected by combining about equimolar amounts of the reactants and a slight excess of carbodiimide such as dicyclohexylcarbodiimide. The reaction proceeds readily at room temperature and is generally completed in about 4 to 20 hours. After the reaction is terminated, the reaction mixture can be filtered to remove the by-product by dicyclohexylurea, and the solvent can be distilled off using a rotary evaporator. The residue can be directly crystallized from a suitable solvent such as benzene/ether or the residue can be chromatographed and the desired material isolated from the appropriate chromatographic fractions. If the basic esters are obtained, the acid addition salts such as those named above, if desired, can be prepared by methods well known in the art.

Compounds wherein $R_4$ is

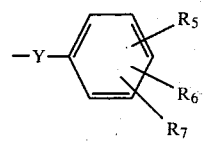

can be prepared according to the following reaction scheme:

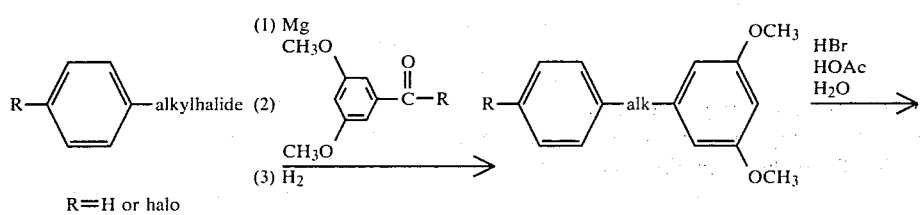

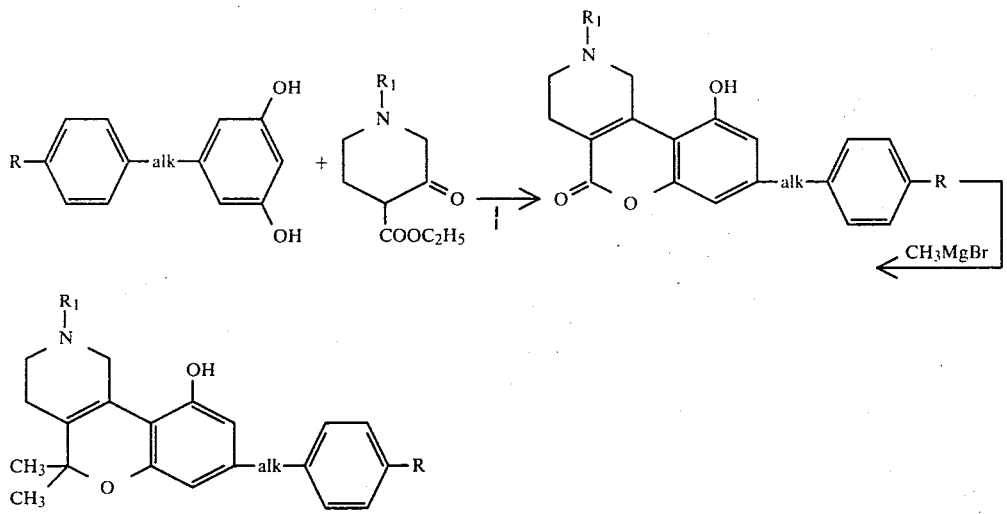

Compounds of formula II wherein $R_3$ is hydrogen and X is $NR_4$ where $R_4$ is alkyl or cycloalkyl can be prepared according to the method described in U.S. Pat. No. 3,576,798.

Compounds of formula III can be prepared according to the method described in U.S. Pat. No. 3,493,579.

The compounds that are effective as antiglaucoma agents according to the present invention include:

(A) 5,5-Dimethyl-10-hydroxy-8-(3-methyl-2-octyl)-2-(2-propynyl)-1,2,3,4-tetrahydro-5H-[1] benzopyrano [3,4-d] pyridine.

(B) 5,5-Dimethyl-10-[4-(1-piperidine)butyryloxy]-8-(3methyl-2-octyl)-2-(2-propynyl)-1,2,3,4-tetrahydro-5H-[1]benzopyrano[3,4-d]pyridine hydrochloride.

(C) 4,4-Dimethyl-9-[(4-homopiperidino) butyryloxy]-7-(3-methyl-2-octyl)- 1,2,3,4-tetrahydrocyclopenta[c][1]benzopyran hydrochloride.

(D) 5,5-Dimethyl-10-[α-methyl-1-piperidinebutyryloxy]- 8-(3 methyl-2-octyl)-2-(2-propynyl)-1,2,3,4-tetrahydro-5H-[1]benzopyrano[3,4-d].

(E) 5,5-Dimethyl-10-[2-methyl-(2-methylpiperidino) butyryloxy]-8-(3-methyl-2-octyl)-2-(2-propynyl)-1,2,3,4-tetrahydro-5H-[1]benzopyrano[3,4-d]pyridine dihydrochloride.

(F) 5,5-dimethyl-10-hydroxy-8-[5-(4-fluorophenyl)-2-pentyl]-2-(2-propynyl)-1,2,3,4-tetrahydro-5H-[1]benzopyrano[2,3-d]-pyridine.

(G) 1,4-ethano-5-oxo-10-[4-(1-piperidino)butyryloxy]-8-(3-methyl-2-octyl)-1,2,3,4-tetrahydro-5H[1]benzopyrano[3,4-d]-pyridine hydrochloride.

(H) 4-oxo-9-[1-(morpholine)butyryloxy]-7-(3-methyl-2octyl)-1,2,3,4-tetrahydrocyclopenta[c][1]benzopyran hydrochloride.

(I) 5,5-Dimethyl-8-[5-(4-fluorophenyl)-2-pentyl]10-[4-(4-morpholine)-butyryloxy]- 2-(2-propynyl)-1,2,3,4-tetrahydro-5H-[1]benzopyrano[3,4-d]pyridine hydrochloride.

(J) 5,5-Dimethyl-8-[5- (4-fluorophenyl)-2pentyl]-10-[α-methyl-4-(morpholino)butyryloxy]-2-(2-propynyl)-1,2,3,4-tetrahydro-5H-[1]benzopyrano[3,4-d]pyridine dihydrochloride.

The following examples illustrate the activity of the compounds useful in the practice of this invention.

EXAMPLE 1

Effect of Topical Application Of the Present Compounds

In this test, unanesthetized male albino rabbits, weighing from 2-4 kg., were used and placed in plexiglass restrainers (Plas Labs Model XPL-502-AR). Then, the eyes of the rabbits were anesthetized by a topical administration of a 1% solution of lidocaine hydrochloride (approximately 0.1 ml.), and the intraocular pressure of the various compounds was measured with a Bausch and Lomb Applamatic Tonometer. The test compounds were instilled topically into the rabbit eye after first being dissolved in distilled water and in a 50% solution of propylene glycol in water. A volume of 0.1 ml. of a 0.1% solution was the amount administered. Each compound was tested in at least 4 eyes from 4 different rabbits. The results are shown below in Table I, where the present compounds are compared with pilocarpine and epinephrine.

TABLE I

| EFFECTS OF TOPICALLY APPLIED COMPOUNDS ON INTRA-OCULAR PRESSURE IN RABBITS | | | | | | |
|---|---|---|---|---|---|---|
| | Solution | Percent Change At | | | | |
| Compound | (%) | 30 Min. | 60 Min. | 90 Min. | 120 Min. | 180 Min. |
| Pilocarpine | 0.1 | +6.0 | +6.6 | +6.6 | +6.6 | −1.3 |
| Epinephrine | 0.1 | +14.8 | +3.4 | +12.3 | −2.5 | −1.5 |
| (B) | 0.1 | −15.4 | −26.9 | −38.5 | −50.0 | −30.8 |
| (C) | 0.1 | +33.3 | −4.2 | +0.8 | −41.7 | −33.3 |
| (E) | 0.1 | −22.2 | −5.6 | −1.1 | −16.7 | −38.9 |
| (F) | 0.1 | −8.0 | −43.0 | −28.0 | −23.0 | −25.0 |
| (G) | 0.1 | −33.3 | −47.6 | −52.4 | −23.8 | −9.52 |
| (H) | 0.1 | −42.9 | −50.0 | −4.9 | −42.9 | −10.7 |
| (I) | 0.1 | −43.3 | −50.0 | −4.0 | −23.3 | −50.0 |
| (J) | 0.1 | −46.1 | −26.9 | −23.1 | −34.6 | −61.5 |

As is shown in Table I, the compounds of the present invention are active when applied topically more so than the standard or control compounds of pilocarpine and epinephrine. As a basis for activity, it has been found that where the compound is topically applied and there is a reduction in the intra-ocular pressure of 20% or more, the compound is active.

EXAMPLE 2

Effect of Oral Administration of Present Compounds

The procedure in this evaluation was the same as that described in Example 1 except that the compounds were placed into gelatin capsules and administered orally. The results of the evaluation are provided in Table II below.

TABLE II

EFFECTS OF ORALLY ADMINISTERED COMPOUNDS ON INTRA-OCULAR PRESSURE IN RABBITS

| Compound | Dose (mg./kg.) | Percent Change At | | | | |
|---|---|---|---|---|---|---|
| | | 30 Min. | 60 Min. | 90 Min. | 120 Min | 180 Min. |
| (A) | 10.0 | −22.0 | −18.0 | −15 | −5.0 | −18.0 |
| (B) | 10.0 | −9.3 | −6.5 | −11.7 | −2.8 | −23.4 |

We claim:

1. A method of reducing intra-ocular pressure in mammalian patients comprising administering to a glaucoma patient a therapeutic effective amount of a compound of the formula

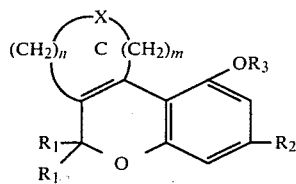

wherein, in the C ring, X is $CH_2$ or

n is an integer of 0 to 3 and m is an integer of 0 to 3; each $R_1$ is loweralkyl and when taken together the substituents $R_1R_1$ form oxygen; $R_2$ is a $C_1$-$C_{20}$ straight or branched chain alkyl, cycloalkyl, or

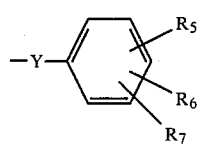

wherein Y is a straight or branched chain alkylene group having from 1 to 10 carbon atoms, and each $R_5$, $R_6$ and $R_7$ are the same or different members selected from the group consisting of H, halo and loweralkyl; $R_3$ is

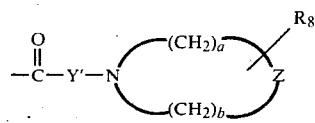

wherein Y' is a straight or branched chain alkylene group having 1 to 8 carbon atoms, a is an integer from 1 to 4, b is an integer from 1 to 4, Z is $CH_2$, O, S or $NR_9$ where $R_9$ is H or loweralkyl, with the provision that when Z is O, S or $NR_9$, the sum of a and b is 3 or 4, and $R_8$ is H or loweralkyl; and the pharmaceutically acceptable salts thereof.

2. A method according to claim 1, wherein X is $CH_2$; n is 2, m is 0; $R_1$ is $CH_3$; $R_2$ is

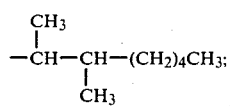

and $R_3$ is

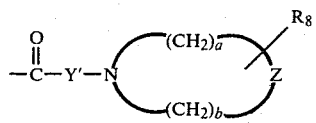

where Y' is $(CH_2)_3$, a is 2, b is 3, Z is $CH_2$ and $R_8$ is H.

3. A method according to claim 1, wherein X is $CH_2$; n is 2, m is 0; $R_1R_1$ is O; $R_2$ is

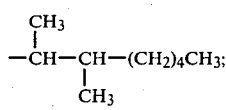

and $R_3$ is

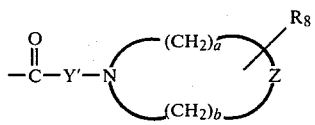

wherein Y' is $(CH_2)_3$, a is 2, b is 2, Z is O and $R_8$ is H.

* * * * *